United States Patent
He et al.

(10) Patent No.: US 8,908,100 B2
(45) Date of Patent: Dec. 9, 2014

(54) ARRANGEMENT AND APPROACH FOR MOTION-BASED IMAGE DATA PROCESSING

(75) Inventors: Haiyan He, Saratoga, CA (US); Johan Gerard Willem Maria Janssen, San Jose, CA (US); Erwin Ben Bellers, Fremont, CA (US)

(73) Assignee: Entropic Communications, Inc., San Diego, CA (US)

( * ) Notice: Subject to any disclaimer, the term of this patent is extended or adjusted under 35 U.S.C. 154(b) by 478 days.

(21) Appl. No.: 12/747,885

(22) PCT Filed: Dec. 26, 2008

(86) PCT No.: PCT/IB2008/055544
§ 371 (c)(1),
(2), (4) Date: Sep. 27, 2010

(87) PCT Pub. No.: WO2009/083925
PCT Pub. Date: Jul. 9, 2009

(65) Prior Publication Data
US 2011/0022418 A1 Jan. 27, 2011

Related U.S. Application Data

(60) Provisional application No. 61/017,448, filed on Dec. 28, 2007.

(51) Int. Cl.
*H04N 5/21* (2006.01)
*G06Q 40/08* (2012.01)
*G06Q 50/24* (2012.01)

(52) U.S. Cl.
CPC ............... *G06Q 40/08* (2013.01); *G06Q 50/24* (2013.01)
USPC ......................................... 348/607; 348/624

(58) Field of Classification Search
USPC .......... 384/448, 607; 382/261, 263, 264, 254, 382/255, 260, 262, 265, 266, 273, 275; 348/448, 607, 624, 625, 630, 705, 706
IPC ................................................ H04N 5/21,5/268
See application file for complete search history.

(56) References Cited

U.S. PATENT DOCUMENTS 5,134,480 A * 7/1992 Wang et al. ................... 348/620
5,649,031 A * 7/1997 Nakamura et al. ............ 382/254
(Continued)

FOREIGN PATENT DOCUMENTS

EP 0657860 A2 6/1995
EP 177939 A1 4/2007
(Continued)

OTHER PUBLICATIONS

Michiel Klompenhouwer and Leo Velthoven, "LCD Motion Blur Reduction with Motion Compensated Inverse Filtering," 2004, SID 04 Digest, pp. 1340-1343.*

(Continued)

*Primary Examiner* — Sherrie Hsia
(74) *Attorney, Agent, or Firm* — Richard Bachand; Duane Morris LLP

(57) ABSTRACT

Image data is processed to present a pleasing display. According to an example embodiment, each pixel of an input video frame is filtered using a variable frequency response filter that is responsive to the motion velocity of the pixel being filtered (e.g., filters data above or below a threshold based upon the motion velocity). A peaked video frame and a blurred video frame are generated for each input video frame using the filtered pixels.

19 Claims, 3 Drawing Sheets

(56) References Cited

U.S. PATENT DOCUMENTS

| | | | |
|---|---|---|---|
| 5,903,680 A * | 5/1999 | De Haan et al. | 382/265 |
| 6,314,160 B1 * | 11/2001 | Dhawale et al. | 378/98.2 |
| 6,347,153 B1 * | 2/2002 | Triplett et al. | 382/224 |
| 6,545,740 B2 * | 4/2003 | Werner | 352/50 |
| 6,810,082 B1 * | 10/2004 | Shen et al. | 375/240.2 |
| 6,930,676 B2 * | 8/2005 | De Haan et al. | 345/204 |
| 7,085,427 B2 * | 8/2006 | Chujoh et al. | 382/263 |
| 7,542,620 B1 * | 6/2009 | Bilbrey et al. | 382/268 |
| 7,769,089 B1 * | 8/2010 | Chou | 375/240.29 |
| 7,856,055 B2 * | 12/2010 | Zhou et al. | 375/240.12 |
| 7,944,508 B1 * | 5/2011 | Chou | 348/624 |
| 8,098,333 B2 * | 1/2012 | Poon | 348/607 |
| 2001/0035969 A1 * | 11/2001 | Kishimoto | 358/1.9 |
| 2002/0171759 A1 * | 11/2002 | Handjojo et al. | 348/452 |
| 2003/0006991 A1 * | 1/2003 | De Haan et al. | 345/473 |
| 2004/0075764 A1 * | 4/2004 | Law et al. | 348/448 |
| 2004/0105029 A1 * | 6/2004 | Law et al. | 348/448 |
| 2005/0162566 A1 * | 7/2005 | Chuang et al. | 348/714 |
| 2005/0168492 A1 * | 8/2005 | Hekstra et al. | 345/690 |
| 2005/0248553 A1 * | 11/2005 | Feng et al. | 345/204 |
| 2006/0146187 A1 * | 7/2006 | Handjojo et al. | 348/448 |
| 2006/0274204 A1 * | 12/2006 | Kimura et al. | 348/624 |
| 2007/0052860 A1 * | 3/2007 | Matsubara et al. | 348/624 |
| 2007/0126678 A1 * | 6/2007 | Shih et al. | 345/89 |
| 2007/0140346 A1 * | 6/2007 | Chen et al. | 375/240.16 |
| 2008/0069217 A1 * | 3/2008 | Minami et al. | 375/240.15 |
| 2009/0060370 A1 * | 3/2009 | Pedersen | 382/261 |
| 2009/0226110 A1 * | 9/2009 | Chen et al. | 382/263 |
| 2010/0098349 A1 * | 4/2010 | Arashima et al. | 382/263 |
| 2010/0189373 A1 * | 7/2010 | Ayzenberg | 382/266 |
| 2011/0019095 A1 * | 1/2011 | He et al. | 348/607 |

FOREIGN PATENT DOCUMENTS

| | | |
|---|---|---|
| JP | 2002351382 A | 12/2002 |
| WO | 2007/116370 A1 | 10/2007 |
| WO | 2008/018006 A2 | 2/2008 |

OTHER PUBLICATIONS

JPO 2002-351382,Dec. 2002, Machine Language Translation, pp. 1-9.*

PCT Search Report mailed on Apr. 17, 2009 corresponding to the related PCT Patent Application No. IB2008/55544.

* cited by examiner

ARRANGEMENT AND APPROACH FOR MOTION-BASED IMAGE DATA PROCESSING

CROSS REFERENCE TO RELATED APPLICATIONS

This application is a National Stage of International Application No. PCT/IB2008/055544, filed Dec. 26, 2008, which claims priority from U.S. Provisional Patent Application No. 61/017,448, filed Dec. 28, 2007. Each patent application identified above is incorporated here by reference in its entirety to provide continuity of disclosure.

The present invention relates generally to image applications, and more specifically, to circuits and methods for processing image data for display.

Many image and video display devices are susceptible to undesirable characteristics that relate to the presentation of video such as motion pictures and, where appropriate, video images that are accurate and pleasing. For instance, liquid crystal display (LCD) displays have suffered from motion blur that can be caused by a relatively slow response time of liquid crystal material in the display, and the hold time of the picture being displayed.

With early LCD panels, motion blur was dominated by the slow reaction time of the LCD panels. With the developing of new liquid crystal (LC) material and related overdrive technology, the reaction time of LC has become much faster. For current LCD displays, motion blur is mainly caused by sample & hold characteristics of the LCD displays, which sample and hold each pixel value for one frame period.

When our (human) eyes track a moving object, the moving object is "still" on our retinas, and we see a sharp image. However, when our eyes track a moving object on a LCD panel, the object is stationary for a frame period. The perceived image is similar to the image of watching a moving object by fixed eyes. Therefore, the perceived image is blurred. To address this issue, LCD panels use high frame rates to achieve a relatively shorter holding time.

In many applications, standard LCD displays (e.g., televisions) use a 100/120 Hz frame rate (100/120p). However, the frame rate of broadcast TV (television) signals are much lower, often broadcast at 50i/60i, while digital TV signals are broadcast at 50i/60i or 50p/60p. Since LCD displays are a progressive display, if the input is an interlaced signal, it must be converted to a progressive signal, so a 50/60p video signal is used. There are different approaches to convert 50/60p video signals into 100/120p video signals. For high-end products, motion compensated frame rate upconversion is commonly used to generate high frame rate video signals. Motion compensated frame rate upconversion calculates each pixel of the temporal new frame using, for example, a weighted average of motion compensated pixels from two or more existing temporal neighboring frames.

The cost of the motion compensated frame rate upconversion can be too high for the middle and low end products. Therefore, low cost approaches have been proposed for the middle and low market segments, such as Black Frame Insertion, Grey Frame Insertion and Dynamic Frame Insertion (DFI). Among above existing low cost approaches, DFI has generally exhibited desirable quality.

In some DFI approaches, the frame rate of a video stream is doubled by sequentially showing blurred and peaked pictures (images). The blurred and peaked pictures are created such that the average of the peaked and blurred image is equal to the input picture. Since the sharp details are only present for half of the time, the holding time has effectively been cut in half.

While DFI has been used to successfully reduce motion blur, it can involve 50/60 Hz flick for large stationary areas, introduces artifacts and its performance is highly dependent on the panel quality. For example, DFI can involve 50/60 Hz flick, particularly when applied on a large still region where sharpened and blurred images are shown alternately at 50/60 Hz. For many viewers, this flick (or flicker) can result in an undesirable viewing experience.

In a real system, certain DFI implementations have taken some trade-off approaches to accommodate the limited output range. One approach has involved adding a clipped value back to a low-passed frame. Another approach involves throwing away the clipped value. The first approach is able to keep the perceived output unchanged, but the motion portrayal improvement from DFI is reduced. The second is another way around, losing contrast in bright and dark details.

The quality of DFI is also affected by the dynamic behavior of LCD panel on which it is used, since DFI alternates two sets of frames with completely different spectrum contents. For some LCD panels, if the response time is not short enough or it can not recover from the black value quickly, DFI causes additional artifacts, such as poor black levels (i.e., black areas are less dark), and color leaking at moving edges.

In view of the above, blurring, artefacts and other issues continue to present challenges to the implementation and processing of image data.

Various aspects of the present invention are directed to arrangements for and methods of processing image data in a manner that addresses and overcomes the above-mentioned issues and other issues as directly and indirectly addressed in the detailed description that follows.

According to an example embodiment of the present invention, a video processing arrangement includes a filter circuit and a mixing circuit. The filter circuit filters each pixel of an input video frame and exhibits a variable frequency response that is responsive to the motion velocity of the pixel being filtered. The mixing circuit generates, for each input video frame, a peaked video frame and a blurred video frame using the filtered pixels.

In some embodiments, the frequency response of the filter circuit is set in response to the motion velocity of pixels being filtered to facilitate the filtering of high-frequency components of video data exhibiting relatively high motion velocity. Thus, the high motion content only appears on display for half of the time, effectively reducing the holding time for these components. Such a motion-controlled dynamic frame insertion (MCFI) approach thus adjusts frequency characteristics of a filter (e.g., a low-pass filter) according to the object motion velocity. If the motion velocity is small, there is only a small difference between the blurred and peaked pictures. If the motion velocity is big, the blurred picture is really blurred. Since the amount of modulation is controlled by the object motion velocity, the risk of artifacts is reduced and flicker is reduced or eliminated (e.g., 50/60 Hz flick on large still areas as described above can be eliminated).

According to another example embodiment of the present invention, video is processed as follows. Each pixel of an input video frame is filtered using a variable frequency response that is responsive to the motion velocity of the pixel being filtered. For each input video frame, a peaked video frame and a blurred video frame are generated using the filtered pixels.

The above summary of the present invention is not intended to describe each embodiment or every implementation of the present invention. Other aspects of the invention will become apparent and appreciated by referring to the following detailed description and claims taken in conjunction with the accompanying drawings.

The invention may be more completely understood in consideration of the following detailed description of various embodiments of the invention in connection with the accompanying drawings, in which.

Figure 1:
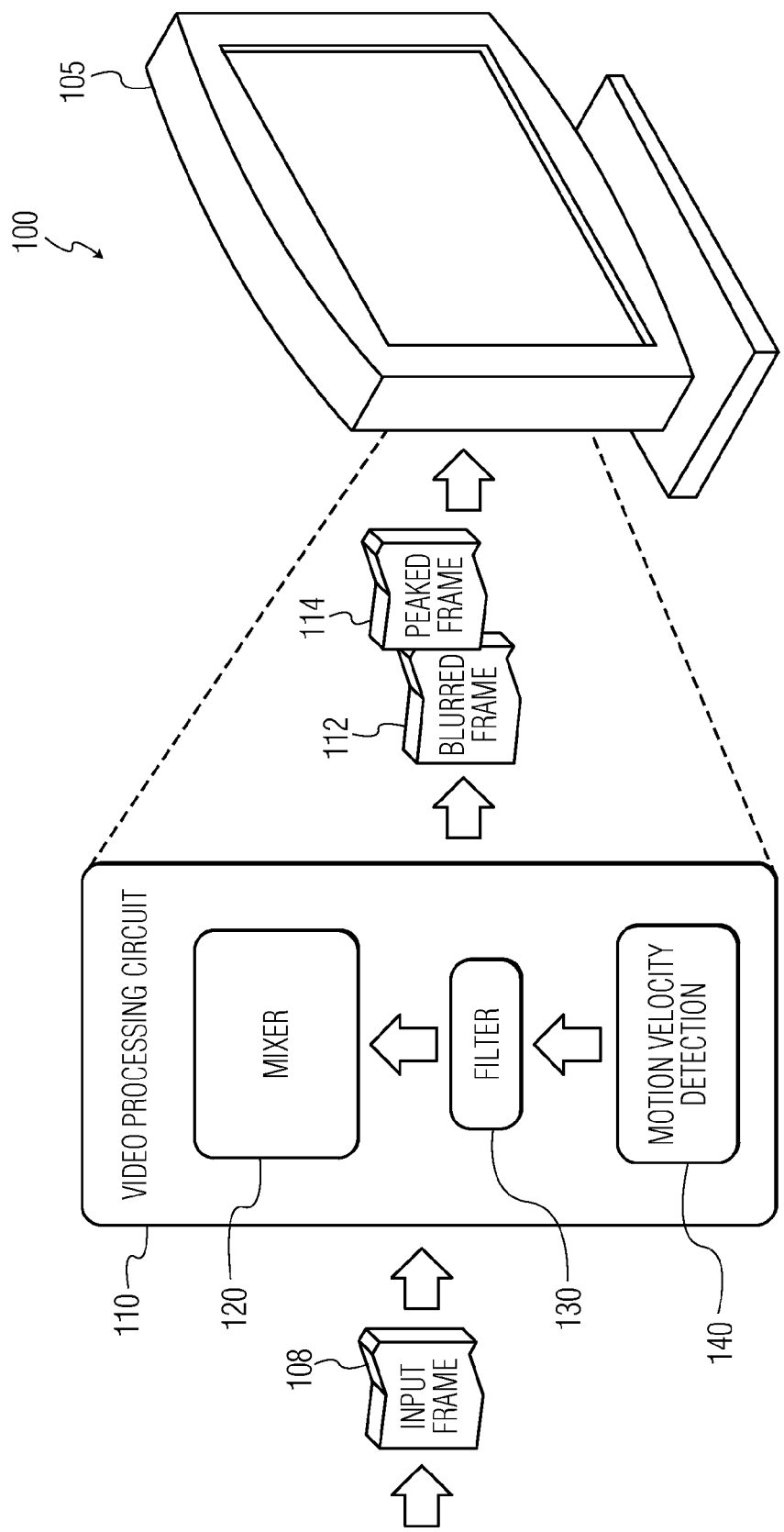
FIG. 1 shows a video display and circuit for processing images in response to motion in video to be displayed, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the invention as defined by the appended claims.

The present invention is believed to be applicable to a variety of arrangements and approaches for image data processing. While the present invention is not necessarily limited to such applications, an appreciation of various aspects of the invention is best gained through a discussion of examples in such an environment.

According to an example embodiment of the present invention, the movement or motion of an object or other item from incoming video images to be displayed is detected from incoming pixels of a video stream. The detected motion is used to set or tune the frequency cutoff of a variable frequency low-pass filter, which is used to filter the incoming video. The filtered output is used to generate video data to be output to the display or screen, such as by mixing or otherwise processing the incoming video together with the filtered output to generate video frames to be displayed.

In some applications, the movement or motion is detected for each pixel, and the low-pass filter is used to filter the particular pixel using a frequency cutoff set in response to the movement or motion detected for that particular pixel. This detection and filtering is carried out for each frame in the incoming video and used to generate alternating peaked and blurred video frames to be output to the display or screen (e.g., with each frame including an array of separately-filtered pixels that make up the entire video frame).

According to another example embodiment of the present invention, video data is provided to a display using a dynamic frame insertion approach. The video data is filtered using a low-pass filter having frequency response that is responsive to the motion velocity of the data being filtered. The filtered video data is used to generate alternating peaked and blurred video frames from each input video frame.

In some applications, the cutoff frequency of the low-pass filter is set relatively higher for video data (i.e., individual pixels or portions of a video image) exhibiting relatively low motion velocity, such as for relatively slow-moving objects. With the cutoff frequency set high, high frequency components of the video data above the frequency cutoff are filtered, such that most (or all) of the video data is passed under most conditions. Therefore, the differences between peaked and still frames are small, and the risk of artifacts is reduced. For still objects and certain embodiments, the low-pass filter can be operated as an all-pass filter, since there is no motion blur for still objects. Therefore, still objects are the same for both the blurred frame and peak frame.

The cutoff frequency for the low-pass filter is set relatively low for high motion video data, as is often common with fast-moving objects. With the cutoff frequency set low, a greater range of frequencies are blocked and less of the video data is passed. Therefore the high motion contents only appears on display for half of the time, effectively reducing the holding time for high-motion contents (e.g., in half), reducing motion blur.

In many applications, one or more of the above approaches is implemented in connection with a dynamic frame insertion approach that is further responsive to color characteristics of the incoming video. For instance, in some applications, the generation of alternating peaked and blurred video frames is reduced or eliminated for near-black and/or near-white video data, in order to reduce the chance of going out of range in a peaked frame. These approaches are used to facilitate the display of video that is pleasing to the human eye.

As may be implemented in connection with one or more example embodiments, peaked video frames are generated in a variety of manners. In many applications, peaking is a type of signal enhancement that is applied to an output video signal before the signal is displayed, and can be used to enhance high frequency edges to enhance the sharpness of a displayed image. For instance, peaked video frames can be generated by adding a video signal value to an input video signal, such as by adding a filtered value of a video frame to the original video frame from which the filtered value was obtained, or by adding some value related to such a filtered value to the original. The peaked video frame can also be generated by subtracting the low-passed frame from an original input frame. Also as may be implemented in connection with one or more example embodiments, blurred video frames are generated by passing low-frequency video data to produce a blurred image, such as by passing less than all image data and/or by passing a low frequency range of video data. For general information regarding peaked video frames, and for specific information regarding approaches to which video frames may be generated in connection with one or more example embodiments, reference may be made to U.S. Pat. No. 6,810,082 assigned to Koninklijke Philips Electronics N.V. (Eindhoven, NL), which is fully incorporated herein by reference. In addition, for general information regarding video processing, and for specific information regarding the generation and use of peaked and blurred video frames (e.g., as used with dynamic frame insertion), reference may be made to International Patent Publication No. WO 2007/088515 A1, entitled "Video Processing Device and Method of Processing Video Data" (having inventor/applicant Tichelaar et. al, c/o NXP Semiconductors), which is, together with the references cited therein, fully incorporated herein by reference.

Turning to the figures, FIG. 1 shows a video display arrangement 100 for processing images in response to motion in video to be displayed, according to another example embodiment of the present invention. The arrangement 100 includes a video display 105 and a video processing circuit 110 that uses input video data 108 to generate output video data 112 and 114 for display. The video processing circuit 110 includes a mixer 120 that generates the output video data (frames) 112 and 114 from the input video data (an input frame) 108 using a filtered output from a filter circuit 130.

The filter circuit 130 filters the input video data using a frequency response that is set or tuned as a function of the motion velocity of the input video data. The motion velocity of the input video data is used to set a cutoff frequency, with the filter circuit 130 filtering incoming video data at frequencies at and/or over the cutoff frequency, passing frequencies below the cutoff frequency. Generally, the filter circuit 130 thus filters high-frequency components of video exhibiting relatively high motion velocity, and passes most or all frequencies of video exhibiting relatively low motion velocity.

The mixer 120 generates and sends successive peaked and blurred video frames 112 and 114 to the display 105 by inserting frames into a video stream provided to the display, using the output of the filter circuit 130 and the incoming video data (frame) 108. This generation of peaked and blurred frames 112 and 114 is carried out for each frame in the video stream, with motion-based filtering carried out for each frame, based upon pixels or other portions of the frame. In some embodiments, the mixer 120 generates the peaked and blurred video frames 112 and 114 on a pixel-by-pixel basis, with different pixels in the image controlled independently from one another for each frame, relative to the type of image data (e.g., blurred or peaked) data inserted into each frame and the motion velocity of each pixel. In this context, each output frame 112 and 114 includes data for an array of pixels making up the frame, with each pixel separately processed.

The input video data 108 is filtered in accordance with the motion velocity of images in the video data using one or more of a variety of approaches. In some applications, the input video data is filtered on a pixel-by-pixel basis, using the motion of each pixel (e.g., the motion of an object, subject or scene in the pixel) to set the frequency response of the filter circuit 130. In other applications, the input video data is filtered using a region or other portion of an image to be displayed (e.g., a portion of a video frame, such as a set of pixels in the video frame), and filtering image data in that region or portion of an image.

In some embodiments, a motion velocity detection circuit 140 detects the motion of the input video data 108 and generates an output to the filter circuit 130. In some applications, the output from the motion velocity detection circuit 140 is used to set the frequency response of the filter circuit for processing the input video data. In other applications, the filter circuit 130 interprets the output from the motion velocity detection circuit 140 and sets the frequency response based upon the interpretation.

The video processing circuit 110 is implemented in one or more of a variety of manners, and in common and/or connected circuits. For example, in some applications, the mixer 120, filter circuit 130 and motion velocity detection circuit 140 are located on a common circuit board, such as those used in video processing pipelines for video display systems such as televisions and computer displays, examples of which are further discussed below.

Figure 2:
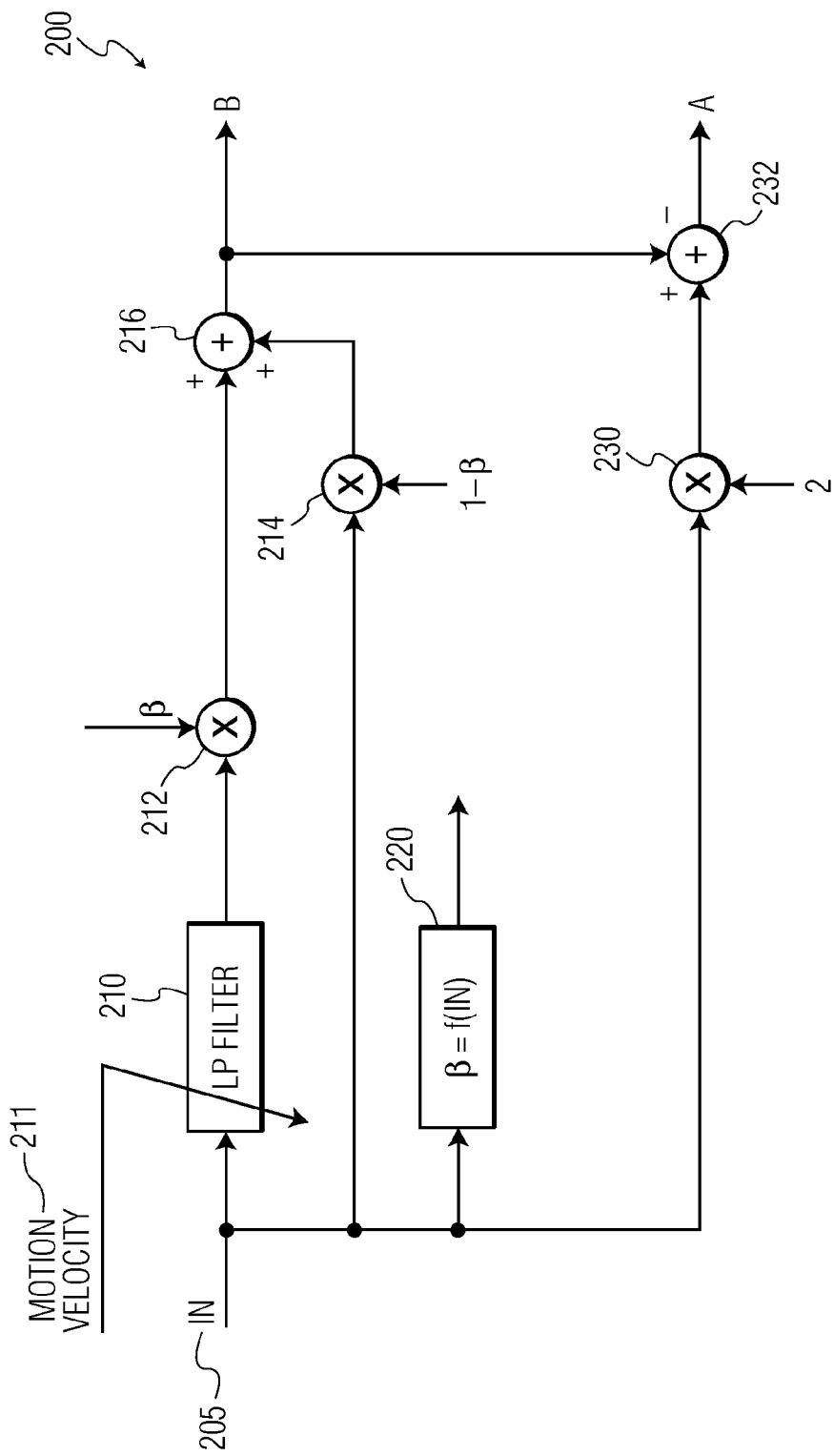
FIG. 2 shows a circuit for processing video data for generating alternating outputs for a display, according to another example embodiment of the present invention.

FIG. 2 shows a video processing circuit 200 for processing video data for generating alternating peaked (at A) and blurred (at B) video frames for a display using a mixing factor denoted as $\beta$, according to another example embodiment of the present invention. Peaked and blurred video frames are respectively output at A and B, using motion characteristics of input video data 205 (IN) as processed in connection with the video circuit 200.

The video circuit 200 includes a low pass filter circuit 210 that generates a filtered output from input video frames 205, using a frequency response that is set in response to the motion velocity (211) of the input video data 205 that is being filtered. Generally, the frequency response of the low pass filter circuit 210 is responsive to the motion velocity 211 such that high-frequency components of incoming video are filtered where the video exhibits relatively high motion velocity.

The video processing circuit 200 also includes a video mixing factor generator 220 that generates mixing factor $\beta$ according to characteristics of the input video being filtered. Generally, the mixing factor $\beta$ is generated in response to the value of the input video (e.g., to the value of each pixel of each video frame) to facilitate the presentation of desirable images from the video data. In this regard, mixing factor $\beta$ is set to zero (0) under input video conditions for which frame insertion is undesirable, and to one (1) under input video conditions amenable to frame insertion. For instance, with certain liquid crystal display (LCD) video displays, the use of a frame insertion approach such as DFI can result in undesirable artefacts for some parts of image, such as near-black and near-white image portions. When a video stream is to be displayed with such an LCD video display, $\beta$ is set to zero (0) for regions and/or pixels in the frame that are not amenable to frame insertion. For other regions in the frame, $\beta$ is set to one (1). Other types of video can be processed using a similar approach, when the video exhibits conditions such as color types or other conditions for which frame insertion is undesirable.

This mixing factor $\beta$ is used at multiplier circuits 212 and 214 in accordance with the following equations depicting the peaked and blurred video frames that are output for each input video frame in connection with certain embodiments:

$$A=(1+\beta)\times IN-\beta\times LP, \quad \text{(Equation 1)}$$

$$B=(1-\beta)\times IN+\beta\times LP \quad \text{(Equation 2)}$$

where
A is the peaked output frame,
B is the blurred output frame,
IN is the input video frame,
LP is the filtered video frame from the low-pass filter 210, and
$\beta$ is the mixing factor that is set as described above.

In consideration of equations 1 and 2 above, when $\beta=1$ for a particular pixel, the blurred output frame is the output from the low-pass filter circuit 210 (i.e., B=LP), which is the filtered value of the pixel obtained using a frequency response set in accordance with the motion velocity of the pixel being filtered. The peaked output frames are the value of twice the input pixel (in a particular frame), less the output from the low-pass filter circuit (i.e., A=2×IN−LP). When $\beta=0$, the peaked and blurred output frames are both at the value of the input pixel, such that frame insertion is effectively not carried out.

In some applications, the circuit 200 is controlled to facilitate the de-blurring of video frames exhibiting objects moving at high speeds, while mitigating the display of artefacts for video frames exhibiting relatively low speed objects. The low pass filter circuit 210 is operated as a relatively large filter (i.e., with a relatively low cutoff frequency to filter a significant amount of high-frequency components of incoming video) for video exhibiting objects moving at high speeds. When processing video exhibiting objects moving at relatively slower speeds, the low pass filter 210 is operated as a relatively small filter (i.e., with a relatively high cutoff frequency to pass most or all frequencies in the incoming video). This approach is further used to control the amount of frequency modulation between displayed (peaked and blurred) video frames, effectively reducing the modulation were appropriate in accordance with the above use of the low pass filter circuit 210.

The cutoff frequency of the low pass filter circuit 210 is set to a frequency, relative to the motion velocity of the incoming video, using one or more of a variety of approaches. For instance, in some applications, the cutoff frequency is set to a value above which artefacts have been known to be present for a particular type of display for which the circuit 200 is used, respectively for pixels exhibiting low or high motion velocities.

Referring to Equations 1 and 2 above and/or the figures and their corresponding description, certain embodiments employ similar approaches with slightly or significantly different equations to generate output video frames in accordance with the present invention. For instance, a certain approach to generating a peaked and/or blurred video frame involves using a high pass filter instead of or in addition to a low pass filter, with a cutoff frequency that is set in accordance with that described above with a low pass filter to effect the generation of video frames in a similar manner. Referring to Equation 1, such an approach can be used with a peaked video frame output generated by adding the input signal with the value of the mixing factor β multiplied by the output from a high pass filter.

In still other embodiments, the mixing factor β is set to a value other than zero or one as described above. For instance, the mixing factor β can be set to 0.5 or some other value that is less than 1 for pixels that are near-black or near-white. In this regard, when a dynamic frame insertion (DFI) approach is carried out; peaked and blurred outputs as generated via Equations 1 and 2 are generated using β=0.5 and thus having a difference that is reduced, relative to the outputs generated when β=1.

Figure 3:
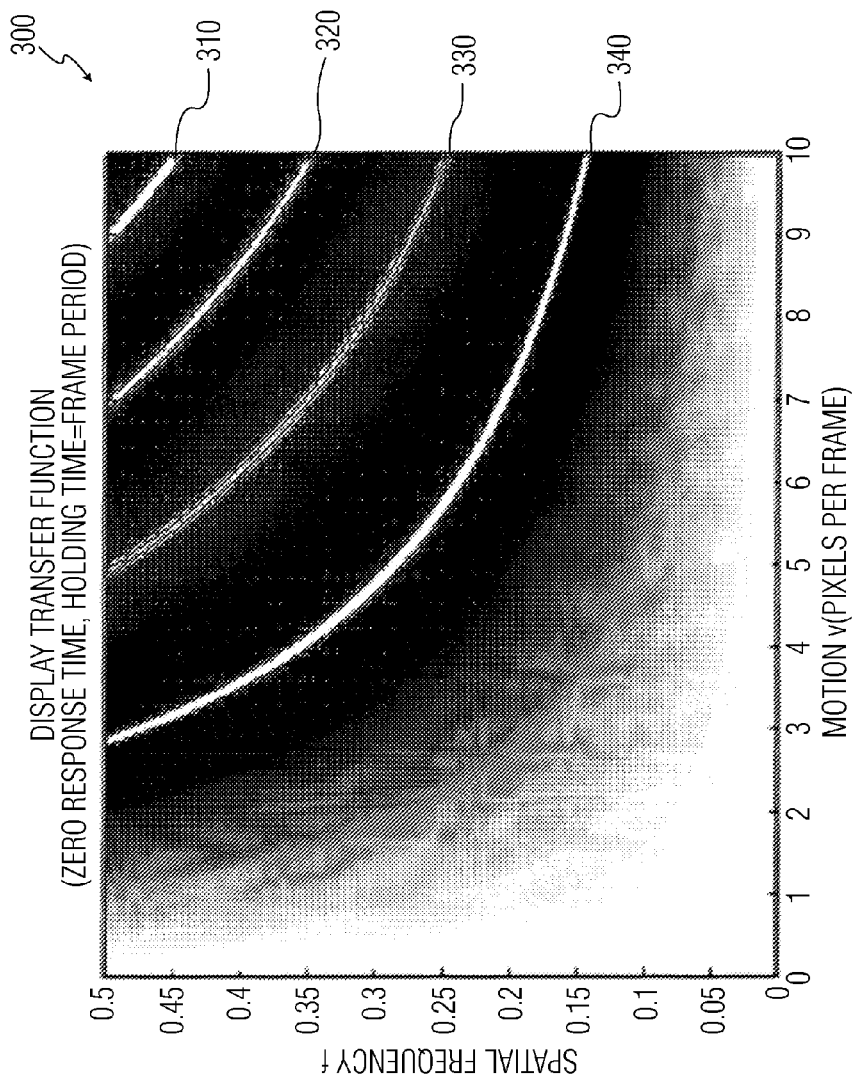
FIG. 3 shows plotted values depicting a relationship between motion blur and motion velocity as used to process image data, in accordance with various example embodiments of the present invention.

FIG. 3 shows plotted values depicting a relationship between motion blur and motion velocity as used to process image data in accordance with various example embodiments of the present invention. Plots 310, 320, 330 and 340 respectively show plots of motion (pixels per frame) on the horizontal axis and spatial frequency on the vertical axis, for example video data in which motion blur occurs as plotted. In these plots, motion blur occurs at lower spatial frequencies as the motion velocity increases. In this regard, various embodiments of the present invention set the frequency response of a video data filter (e.g., the filter 130 in FIG. 1) to filter frequencies above the indicated values frequencies, relative to motion velocity values, using one or more of the plots 310-340.

The display approaches and embodiments described herein are amenable to use with a multitude of different types of display systems and arrangements, and can be arranged and/or programmed into a variety of different circuits and controllers. For example, certain embodiments involve processing approaches that are carried out in a video processing circuit pipeline for video or television (TV) systems. One such embodiment involves the implementation of one or more of the above frame insertion approaches with a backend video scaler integrated circuit, such as those used on the signal board of an LCD display or television. Another embodiment involves the implementation of one or more of the above frame insertion approaches with a timing controller circuit, such as those used on the panel of a LCD display for controlling the sequencing and timing of image signals. These applications are implemented using motion-based filtering of video data to be displayed in a manner that mitigates undesirable display characteristics, such as those described in the background above.

In addition to the above, the various processing approaches described herein can be implemented using a variety of devices and methods including general purpose processors implementing specialized software, digital signal processors, programmable logic arrays, discrete logic components and fully-programmable and semi-programmable circuits such as PLAs (programmable logic arrays).

The various embodiments described above and shown in the figures are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For example, various image data processing approaches may be amenable to use with various display types, relating to projection displays, flat-panel displays, LCD displays (including those described) involving flat-panel or projection display approaches, and other digital light processing display approaches. Such modifications and changes do not depart from the true scope of the present invention that is set forth in the following claims.

What is claimed is:

1. A video processing arrangement comprising:
    a filter circuit to filter each pixel of an input video frame, the filter circuit having a variable frequency response that is responsive to a motion velocity of the pixel being filtered; and
    a mixing circuit, coupled to the filter circuit, to generate, for each input video frame, a peaked video frame and a blurred video frame using each of the filtered pixels.

2. The arrangement of claim 1, wherein the filter circuit filters each pixel to control the frequency modulation between successive peaked and blurred video frames generated for each input video frame.

3. The arrangement of claim 1, further including a motion detection circuit to detect the motion velocity of each input pixel and to provide an output indicative of the motion velocity of each input pixel to the filter circuit, wherein the filter circuit uses the motion velocity output for a particular pixel to set the variable frequency response for use in filtering the particular pixel.

4. The arrangement of claim 1, wherein the mixing circuit generates, for each incoming video frame in a video stream, peaked and blurred video frames that respectively include an array of pixels that are individually filtered by the filter circuit and processed by the mixing circuit.

5. The arrangement of claim 1, wherein the filter circuit filters each pixel of an input video frame by filtering each pixel to control an amount of frequency modulation between consecutive peaked and blurred image frames generated from each pixel by the mixer.

6. The arrangement of claim 1, wherein the filter circuit uses a low-pass filter set to a relatively high frequency cutoff to filter pixels exhibiting a relatively low motion velocity, and uses a low-pass filter set to a relatively low frequency cutoff to filter pixels exhibiting relatively high motion velocity.

7. The arrangement of claim 1, wherein the filter circuit passes pixel data having a frequency that is below a frequency cutoff value that is inversely proportional to the motion velocity of the pixel being filtered.

8. The arrangement of claim 1, wherein the filter circuit controls the amount of frequency modulation between the peaked and blurred video frames generated from a particular input video frame by
    filtering pixels having a high motion velocity with a large spatial filter, and
    filtering pixels having a relatively low motion velocity with a small spatial filter.

9. The arrangement of claim 1, wherein
    the filter circuit filters each pixel of an input video frame by generating a filtered pixel value (LP) for each pixel, and the mixing circuit generates a peaked video frame and a blurred video frame using the filtered pixels and a mixing factor β that is set as a function of a color characteristic of the input pixel, by:
generating and outputting a peaked video frame including a pixel having a value that is equal to (1+β)×IN−β×LP, and
generating and outputting a blurred video frame including a pixel having a value that is equal to (1−β)×IN+β×LP.

10. A method for processing video, the method comprising:
filtering each pixel of an input video frame using a variable frequency response that is responsive to a motion velocity of the pixel being filtered; and
generating, for each input video frame, a peaked video frame and a blurred video frame using each of the filtered pixels.

11. The method of claim 10, wherein the filter circuit filters each pixel to control the frequency modulation between successive peaked and blurred video frames generated for each input video frame.

12. The method of claim 10, further including
detecting the motion velocity of each input pixel and providing an output indicative of the motion velocity of each input pixel to the filter circuit, and
using the motion velocity output for a particular pixel to set the variable frequency response for use in filtering the particular pixel.

13. The method of claim 10, wherein generating, for each input video frame, a peaked video frame and a blurred video frame using the filtered pixels includes generating peaked and blurred video frames that respectively include an array of pixels that are individually filtered and processed.

14. The method of claim 10, wherein filtering each pixel of an input video frame includes filtering each pixel to control an amount of frequency modulation between consecutive peaked and blurred image frames generated from each pixel.

15. The method of claim 10, wherein filtering each pixel of an input video frame includes using a low-pass filter set to a relatively high frequency cutoff to filter pixels exhibiting a relatively low motion velocity, and using a low-pass filter set to a relatively low frequency cutoff to filter pixels exhibiting relatively high motion velocity.

16. The method of claim 10, wherein filtering each pixel of an input video frame includes passing pixel data having a frequency that is below a frequency cutoff value that is inversely proportional to the motion velocity of the pixel being filtered.

17. The method of claim 10, wherein filtering each pixel of an input video frame includes controlling the amount of frequency modulation between the peaked and blurred video frames generated from a particular input video frame by
filtering pixels having a high motion velocity with a large spatial filter, and
filtering pixels having a relatively low motion velocity with a small spatial filter.

18. The method of claim 10, wherein
filtering each pixel of an input video frame includes generating a filtered pixel value (LP) for each input pixel (IN), and
generating a peaked video frame and a blurred video frame using the filtered pixels includes using the filtered pixels and a mixing factor β that is set as a function of a color characteristic of the input pixel and
generating and outputting a peaked video frame including a pixel having a value that is equal to (1+β)×IN−β×LP, and
generating and outputting a blurred video frame including a pixel having a value that is equal to (1−β)×IN+β×LP.

19. An arrangement for processing video, the arrangement comprising:
means for filtering each pixel of an input video frame using a variable frequency response that is responsive to a motion velocity of the pixel being filtered; and
means for generating, for each input video frame, a peaked video frame and a blurred video frame using each of the filtered pixels.

* * * * *